United States Patent [19]

Henkelmann et al.

[11] Patent Number: 5,711,863
[45] Date of Patent: Jan. 27, 1998

[54] MEASURING-PROBE ARRANGEMENT IN A GAS CONDUIT

[75] Inventors: Konrad Henkelmann, Friolzheim; Romuald Fries, Ditzingen, both of Germany

[73] Assignee: Robert Bosch GmbH, Stuttgart, Germany

[21] Appl. No.: 530,163

[22] PCT Filed: May 11, 1994

[86] PCT No.: PCT/DE94/00536

§ 371 Date: Sep. 29, 1995

§ 102(e) Date: Sep. 29, 1995

[87] PCT Pub. No.: WO94/28404

PCT Pub. Date: Dec. 8, 1994

[30] Foreign Application Priority Data

Jun. 1, 1993 [DE] Germany ............... 43 18 107.4

[51] Int. Cl.[6] .................................................. G01N 27/46
[52] U.S. Cl. .......................... 204/428; 204/424; 204/427; 204/426; 422/94; 422/98
[58] Field of Search ............................ 204/424, 427, 204/428, 429, 426; 422/94, 98

[56] References Cited

U.S. PATENT DOCUMENTS

| | | | |
|---|---|---|---|
| 4,038,034 | 7/1977 | Nakajima et al. | 204/428 X |
| 4,063,897 | 12/1977 | Aoki | 204/428 X |
| 4,096,050 | 6/1978 | Kobayashi et al. | 204/428 |
| 4,123,131 | 10/1978 | Pearce et al. | 204/428 X |
| 4,132,615 | 1/1979 | Linder et al. | 204/428 |
| 4,200,511 | 4/1980 | Sato et al. | 204/428 |
| 4,240,890 | 12/1980 | Watanabe et al. | 204/195 S |
| 4,437,971 | 3/1984 | Csanitz et al. | 204/427 |
| 4,502,939 | 3/1985 | Holfelder et al. | 204/429 |
| 4,526,672 | 7/1985 | Reed | 204/428 |
| 4,569,748 | 2/1986 | Yamakawa et al. | 204/429 |
| 4,591,422 | 5/1986 | Kato et al. | 204/426 |
| 4,756,885 | 7/1988 | Raff et al. | 422/98 |
| 4,897,174 | 1/1990 | Wang et al. | 204/425 |
| 5,049,255 | 9/1991 | Wolfe et al. | 204/428 |
| 5,324,415 | 6/1994 | Blumenthal et al. | 204/427 |
| 5,329,806 | 7/1994 | McClanahan et al. | 73/436 |
| 5,389,223 | 2/1995 | Hoetzel | 204/425 |
| 5,616,825 | 4/1997 | Achey et al. | 204/426 X |

*Primary Examiner*—Harold Y. Pyon
*Attorney, Agent, or Firm*—Spencer & Frank

[57] ABSTRACT

The invention proposes a measuring-probe arrangement for detecting gases flowing in a gas conduit, especially exhaust gases flowing in an exhaust conduit of internal combustion engines. The measuring-probe arrangement has a measuring element (13) which is surrounded in sealing fashion by a housing (11). The section of the measuring element (13a) located at the measured-gas end of the measuring-probe projects from the housing (11) and is surrounded with a clearance by a protective tube (21) which is fixed by one end section on the housing (11) and has one or more openings (22) for the measured gas. The measuring probe (10) is arranged in such a way in the gas conduit (30) that the gas opening (22) is arranged on that side of the protective tube (21) which faces away from the flow (35) of the measured gas.

1 Claim, 1 Drawing Sheet

5,711,863

MEASURING-PROBE ARRANGEMENT IN A GAS CONDUIT

This application is a 371 of PCT/DE94/00536, filed May 11, 1994, published as WO94/28404 Dec. 8, 1994.

BACKGROUND OF THE INVENTION

The invention takes as its starting point a measuring-probe arrangement for detecting measured gases flowing in a gas conduit. In the known measuring-probe arrangements (U.S. Pat. No. 4,756,885), a protective tube is provided, surrounding which surrounds a clearance that section of a measuring element composed essentially of ceramic material which projects from a tubular housing at the measured-gas end. The bottom of the protective tube at the measured-gas end has a gas opening to allow the measured gas to be fed to the measuring probe. To allow flow through the protective tube, a plurality of outlet openings are provided for the emergence of the measured gas in the side wall of the protective tube near to the measured-gas end of the housing. However, this arrangement of the inlet opening and the outlet openings does not prevent measured gas from entering the protective tube through the outlet openings, some of which face in a direction opposite to the direction of flow of the measured gas, and, as a result, the condensation water which forms particularly in exhaust systems of internal combustion engines reaches the ceramic measuring element. If the condensation water comes into contact with the heated ceramic of the measuring element, the temperature shock can give rise to cracks in the ceramic which can ultimately lead to the failure of the measuring element. The known measuring probes are furthermore screwed into the gas conduit by means of a thread arranged on the housing of the measuring probe. As a result, directional installation is not possible, and the gas openings in the protective tube may face in any direction.

SUMMARY AND ADVANTAGES OF THE INVENTION

The measuring-probe arrangement according to the invention, has a measuring element with a section, known as the measured-gas end, projecting from a housing into an opening in the gas conduit. The measured-gas end is surrounded by a protective tube having at least one gas opening. The gas openings are arranged on the side of the protective tube facing away from the direction of gas flow in the gas conduit. The measuring-probe of the invention also has a marking on the region of the measuring-probe outside the gas conduit which indicates the position of the gas opening the invention has the advantage that the condensation water does not reach the ceramic measuring element.

For the correct orientation of the gas openings in the gas conduit, it is particularly advantageous to insert the measuring probe in an adjustable manner. This is expediently achieved by inserting the measuring probe into a flange arranged on the gas conduit and by fastening it with a union nut. The opening in the gas conduit may also have a sealing surface on which a collar on the housing of the measuring-probe rests, creating an airtight seal.

BRIEF DESCRIPTION OF THE DRAWINGS

A preferred embodiment of the invention is illustrated in the drawings and explained in greater detail in the description which follows.

DETAILED DESCRIPTION OF THE PREFERRED EMBODIMENTS

Figure 1:
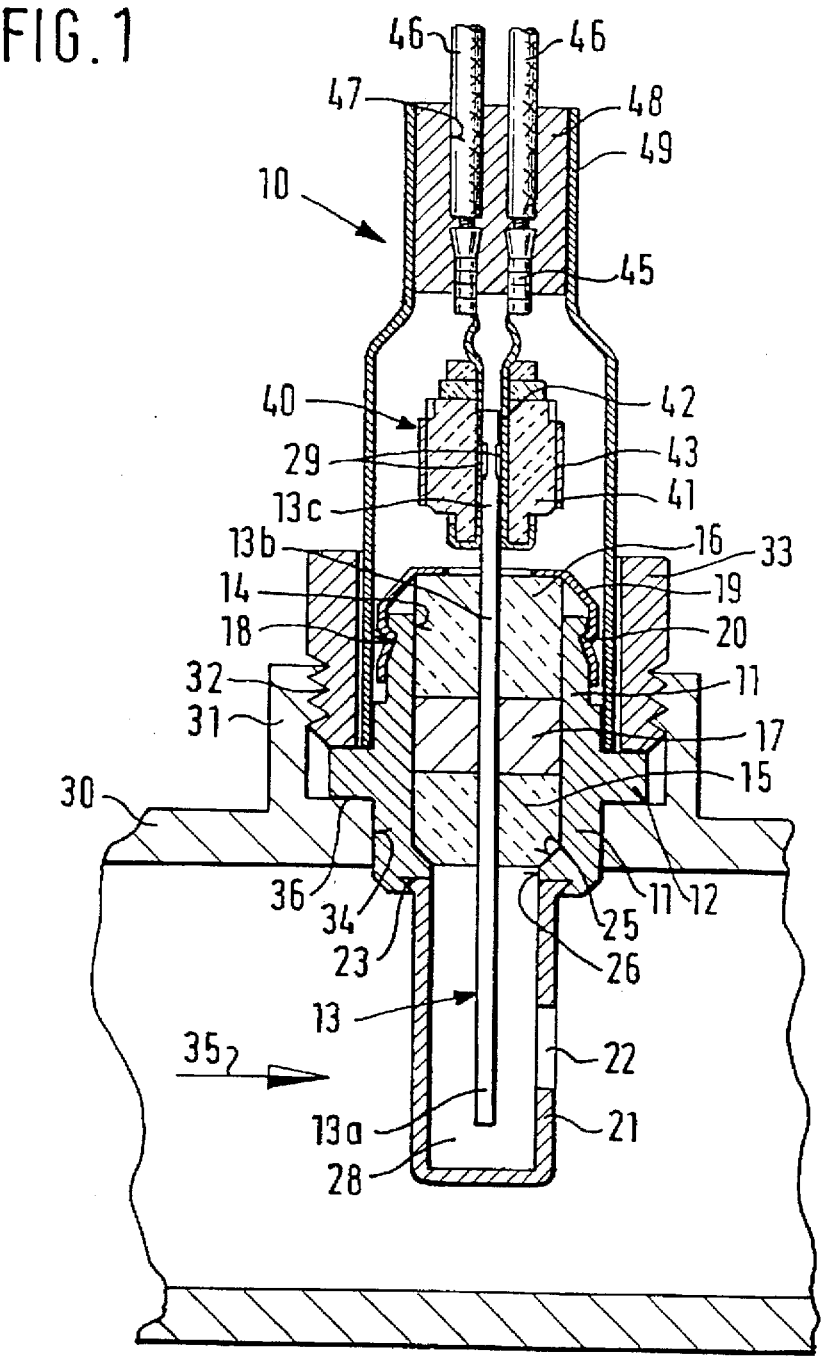
FIG. 1 shows a cross section of the measuring-probe arrangement according to the invention and FIG. 2 shows a section of a protective tube with a plurality of gas openings.

The measuring probe shown in the drawings is a measuring probe 10 for determining the oxygen content in exhaust gases in, for example, an exhaust conduit 30 of an internal combustion engine. The measuring probe 10 has a measuring element 13 which operates on the known principle of oxygen ion conduction by a solid electrolyte. The solid electrolyte used is preferably stabilized zirconium dioxide. In the example under consideration, the measuring element 13 is a planar sensor of laminar construction. However, it is equally conceivable to use a so-called finger sensor formed by a solid-electrolyte tube as the measuring element 13. The measuring element 13 is not illustrated and described here. Reference is made, for example, to German Offenlegungsschrift 3,017,947 (U.S. Pat. No. 4,502,939). It is possible for the measuring element 13 to work in various different ways.

The measuring probe 10 has a tubular metal housing 11 with a longitudinal hole 14 which has a coaxial shoulder 25 which faces away from the measured-gas end of the measuring probe 10 and forms the transition to a hole 26 located at the measured-gas end. At the outer circumference, the metal housing 11 has a radially encircling collar 12. A cup-shaped protective tube 21 with an outward-pointing annular flange 23 is fixed in the hole 26 in the metal housing 11. To allow the gas to enter and leave, the protective tube 21 has a gas opening 22 in its side wall. The space enclosed by the protective tube 21 forms a measuring space 28 for the measuring element 13.

A section 13a of the measuring element 13 at the measured-gas end projects into the measuring space 28 with a clearance relative to the protective tube 21. A section 13b of the measuring element 13 at the connection end is held in electrically insulated fashion in the longitudinal hole 14 in the metal housing 11. For this purpose, there is an electrically insulating ceramic insert 15 at the measured-gas end in the longitudinal hole 14 in the metal housing 11. The ceramic insert 15 rests on the shoulder 25 in the longitudinal hole 14. Resting on the ceramic insert 15 located at the measured-gas end there is a package-like seal 17 which surrounds the measuring element 13, extends up to the wall of the longitudinal hole 14 in the metal housing 11 and is composed of an electrically insulating material such as talc. A connection-end ceramic insert 16 is placed on the seal 17 and this ceramic insert likewise surrounds the measuring element 13 and fills the cross section of the longitudinal hole 14, and also projects from the longitudinal hole 14 in the metal housing 11 at the connection end. Resting on the connection-end end face of the connection-end ceramic insert 16 there is a retaining cap 19, which is under mechanical pressure and which presses the connection-end ceramic insert 16, the seal 17 and the ceramic insert 15 located at the measured-gas end against the shoulder 25 in the longitudinal hole 14 in the metal housing 11. As a counter abutment, the end section of the retaining cap 19 located at the measured-gas end is fixed by means of a snap-in nose 20 in an annular groove 18 on the outside of the metal housing 11.

Projecting beyond the retaining cap 19 is a connection-end end section 13c which, for example, has two contact surfaces 29 (not shown in greater detail). The contact surfaces 29 are connected to conductor tracks (not shown) which, for their part, lead to electrodes and heating conductors (likewise not shown) arranged on the section 13a located at the measured-gas end.

A connector plug 40 is pushed onto the contact surfaces 29. The connector plug 40 is made up of two contact-part carriers 41, contact parts 42 and a spring element 43. The contact-part carriers 41 are electrically insulating components made of ceramic which contain the contact parts 42 provided for the purpose of making contact with the contact surfaces 29. The contact parts 42 are made of sheet metal in strip form. The two contact-part carriers 41 and the connection-end end section 13c of the measuring element 13 arranged between them are surrounded and held together jointly by the ring-like spring element 43. At the connection end, the contact parts 42 are each extended in the form of strips and, in this end section, are designed as terminals 45 for connecting leads 46.

The terminals 45 of the contact parts 42 together with the connecting leads 46 are each tightly enclosed in through holes 47 in a flexible, plug-like molding 48 composed of a heat-resistant material such as PTFE. The molding 48 is surrounded and compressed by a metal sleeve 49. The metal sleeve 49 is pushed onto the metal housing 11 at its opening located at the measured-gas end and is secured on it by welding or the like. The metal sleeve 49 is expediently of step-shaped configuration and has regions of different diameter to match the characteristics of the components of the measuring element 13 which are contained in it.

The exhaust conduit 30 is provided with an opening 34 having a sealing surface 36 which surrounds the opening 34 and which is surrounded by a flange 31 with a thread 32. To fix it, the measuring probe 10 is pushed through the opening 34, thus resting by its collar 12 on the exhaust conduit 30. A union nut 33 is passed over the measuring probe 10 and screwed into the thread 32, pressing the collar 12 of the metal housing 11 onto the sealing surface 36 of the exhaust conduit 30. It is expedient to arrange a sealing ring between the sealing surface 36 and the collar 12 to ensure gastight fastening. The measured gas flows through the exhaust conduit 30 in direction of flow 35.

A marking (not shown) for example is made on the metal sleeve 49 of the measuring probe 10 to indicate the position of the gas opening 22 in the protective tube 21. With the aid of this marking, the measuring probe 10 is inserted into the opening 34 in the exhaust conduit 30 in such a way that the measured gas does not impinge on the gas opening 22. A preferred arrangement is one in which the gas opening 22 faces in the direction of flow 35 of the measured gas.

Once the measuring probe 10 has been given its preferred orientation in the opening 34 in relation to the flow of the measured gas, the measuring probe is fastened to the exhaust conduit 30 by means of the union nut 33. On the other hand, an embodiment is conceivable in which the geometry of the collar 12 is such that mounting is only possible in the correct position, for example by form-fitting means.

Figure 2:
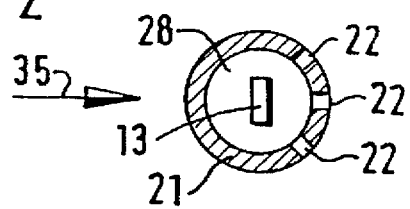

In addition to the embodiment of the protective tube 21 with a gas opening 22 in accordance with the preferred embodiment, an embodiment with a plurality of gas openings 22 is also possible. As shown in FIG. 2, the gas openings 22 are arranged on that side of the protective tube 21 upon which the measured gas does not impinge. This ensures that the exhaust gas, which is laden with condensation water, does not get into the measuring space 28 but is deposited on that wall of the protective tube 21 which faces in the opposite direction to the direction of flow 35. On the other hand, it is quite possible, in order to achieve better flow through the measuring space 28, to make openings in the protected tube 21 which point in the opposite direction to the direction of flow 35, but these should have an extremely small total cross section in order to prevent penetration of condensation water as far as possible.

In addition, it should be mentioned that the term "measuring element 13" is intended to refer, in particular, to gas-measuring elements which determine the lambda value of gas mixtures but that they can also be temperature detectors, moisture sensors, pressure transducers or similar sensors.

We claim:

1. A measuring arrangement for detecting gases flowing in a gas conduit, comprising:

a gas conduit for gases flowing in a given direction, and having an opening in its wall;

a measuring-probe having a housing with a collar, a measuring element having a first portion disposed within said housing and a second portion projecting from said housing into the opening of the gas conduit, a protective tube surrounding said second portion of said measuring element and separated from said second portion by a clearance, said protective tube having at least one gas opening, each of said gas openings positioned to face away from the direction of flow of gases in the gas conduit, and a marking on said housing outside the gas conduit indicating a position of the gas opening in said protective tube; and a fastening means separate from said measuring-probe for securing the measuring-probe to the gas conduit such that the measuring-probe can move radially, said fastening means comprising a flange on the gas conduit at the opening therein having a thread into which a union nut is screwed to engage the collar on said housing and a sealing surface surrounding the opening in the gas conduit on which the collar of said housing rests such that the sealing surface forms a gastight seal at the point of contact with the collar.

\* \* \* \* \*